United States Patent [19]
Plachetka

[11] Patent Number: 5,872,145
[45] Date of Patent: Feb. 16, 1999

[54] FORMULATION OF 5-HT AGONIST AND NSAID FOR TREATMENT OF MIGRAINE

[75] Inventor: John R. Plachetka, Chapel Hill, N.C.

[73] Assignee: Pozen, Inc., Chapel Hill, N.C.

[21] Appl. No.: 907,826

[22] Filed: Aug. 14, 1997

Related U.S. Application Data

[60] Provisional application No. 60/024,129 Aug. 16, 1996.
[51] Int. Cl.$^6$ .......................... A61K 31/405; A61K 31/19; A61K 31/16
[52] U.S. Cl. .......................... 514/415; 514/569; 514/570; 514/629
[58] Field of Search .................................... 514/415, 569, 514/629, 570

[56] References Cited

U.S. PATENT DOCUMENTS

| | | |
|---|---|---|
| 4,024,279 | 5/1977 | Zor et al. . |
| 4,816,470 | 3/1989 | Dowle et al. . |
| 5,360,925 | 11/1994 | Chabrier De Lassauniere et al. ... 560/169 |
| 5,387,604 | 2/1995 | McDonald et al. ...................... 514/456 |
| 5,514,168 | 5/1996 | Friedman .................................. 607/89 |
| 5,605,917 | 2/1997 | Ogletree . |
| 5,607,960 | 3/1997 | Wythes . |
| 5,618,816 | 4/1997 | Crenshaw et al. . |

FOREIGN PATENT DOCUMENTS

| | | |
|---|---|---|
| 2162522 | 8/1985 | United Kingdom . |

OTHER PUBLICATIONS

Anderson, "Double–blind study of naproxen vs placebo in the treatment of acute migraine." (1989); *Cephalalgia*, vol. 9, 29–32.

Baumel, "Migraine: A pharmacological review with newer options and delivery modalities," (1994), *Neurology*, vol. 44Supp3, S13–S17.

Boureau, "Comparison of subcutaneous sumatriptan with usual acute treatments for migraine. French Sumatriptan Group." (1995) *Eur. Neurol.*, vol. 35(5), 264–269.

Bousser, Efficacy of subcutaneous sumatriptanin the acute treatment of early–morning migraine: a placebo–controlled trial. Early–Morning Sumatriptan Study Group (1993) *J Intern Med*, vol. 234(2), 211–216.

Cady, "Treatment of Acute Migraine With Subcutaneous Sumatriptan." (1991) *JAMA*, vol. 265, No. 21, 2831–2835.

Cady, "Efficacy of subcutaneous sumatriptan in repreated episodes of migraine" (1993) *Neurology*, vol. 43, 1363–1368.

Centonze, "Evaluation of the efficacy of oral sumatriptan in the management of migraine attacks. Clinical Results" (1995) *La Clinica Teraputica*, vol. 146(11), 721–728 (Article in the Italian language, Citation to English language abstract only at 727).

Dechant, "Sumatriptan A review of its Pharmacodynamic Properties, and Therapeutic Efficacy in the Acute Treatment of Migraine and Cluster Headache" (1992) *Drugs*, vol. 43(5) 776–798.

Klapper, "Toward a Standard Drug Formulary for the Treatment of Headache" (1995) *Headache*, Apr., 1995, 225–227.

Oral Sumatriptan Group, "Sumatriptan—An Oral Dose–defining Study" (1991) *Eur. Neurol.*, vol. 31, 300–305.

Thomson, "A Study to Compare Oral Sumatriptan with Oral Aspirin plus Oral Metoclopramide in the Acute Treatment of Migraine" (1992) *Eur. Neurol.*, vol. 32, 177–184.

Todd, "Naproxen A reappraisal of its Pharmacology, and Therapeutic Use in Rheumatic Diseases and pain States" (1990) *Drugs*, vol. 40(1), 91–137.

Tokola, "Effects of migraine attack and metoclopramide on the absorption of tolfenamic acid" (1984) *Br. J Clin. Pharmac*, vol. 17, 67–75.

Tokola, "Tolfenamic acid, metoclopramide, caffeine and their combinations in the treatment of migraine attacks" (1984) *Cephalalgia*, vol. 4, 253–263.

*Primary Examiner*—William R. A. Jarvis
*Attorney, Agent, or Firm*—Lorusso & Loud

[57] ABSTRACT

This invention comprises a method of treating migraine in a human comprising co-timely administering of a therapeutically effective amount of a 5-HT agonist coordinated with a therapeutically effective amount of an analgesic, particularly a long-acting NSAID in doses below those ordinarily considered as minimum effective doses as to both 5-HT agonist and long-acting NSAID. Dosage forms are also included herein.

61 Claims, No Drawings

FORMULATION OF 5-HT AGONIST AND NSAID FOR TREATMENT OF MIGRAINE

RELATED APPLICATIONS

This application claims priority from Provisional Application 60/024,129 filed Aug. 16, 1996.

FILED OF THE INVENTION

This invention comprises a method of treating migraine in a human comprising co-timely administering of a therapeutically effective amount of a 5-HT agonist coordinated with a therapeutically effective amount of an analgesic, particularly a long-acting NSAID, and in some instances, doses below those ordinarily considered as minimum effective doses as to one or both 5-HT agonist and long-acting NSAID. Dosage forms are also included herein.

This invention also comprises a unit dosage form comprising a co-timely delivered therapeutically effective amount of a 5HT agonist coordinated and a therapeutically effective amount of an NSAID or non-NSAID analgesic. Particularly noted is the NSAID ibuprofen. The invention further comprises such unit dosage form wherein the NSAID is a long-acting NSAID. In some embodiments of the unit dosage form the 5HT agonist is sumatriptan, optionally in an amount of from about 1 to about 300 mg, and further wherein the amount is about 1 to about 10 mg (particularly adapted to parenteral administration). A long-acting NSAID useful in the unit dosage form is naproxen, or pharmaceutically acceptable salt thereof such as naproxen sodium. Such unit dosage form usefully contains naproxen, or pharmaceutically acceptable salt thereof in an amount of from about 100 mg to about 1500 mg, and particularly in an amount of from about 200 to about 600 mg. A unit dosage form of sumatriptan and naproxen is specifically noted. Such unit dosage form usefully comprises from about 5 to about 100 mg. sumatriptan, and from about 200 to about 600 mg naproxen.

BACKGROUND OF THE INVENTION

The compound 5-hydroxytryptamine (5-HT or 5HT), also known as serotonin or enteramine, is a known vasoactive agent and endogenous neurotransmitter acting on receptors both within and outside the central nervous system and on blood vessels. Drugs acting on these receptors are known as 5-HT agonists or antagonists. These 5-HT receptors have been further classified into several receptor sub-classes, some of which themselves contain sub-types, and are designated, for example, 5-HT1, 5-HT1-like, 5-HT$_{1B}$, 5-HT$_{1D}$, 5-HT2, 5-HT3, and so on.

5-HT1-like agonists and agonists at other 5-HT1 sites comprise a known subclass of therapeutics with a variety of uses, notably including migraine therapy. Representative members of this class of compounds include sumatriptan succinate (distributed under the name Imitrex™ by GlaxoWellcome). Sumatriptan and related 5-HT agonist heterocyclic compounds are described in U.S. Pat. No. 4,816,470 to Dowle et al., the teachings of which are incorporated by reference. Note is made of ergot alkaloids which have 5-HT receptor activity, and these drugs are distinct from sumatriptan and its analogs in their chemical structure. In addition, ergots exhibit additional pharmacological properties distinct from sumatriptan. Ergot alkaloids and related compounds such as dihydroergotamine mesylate (DHE 45) are identified with 5-HT agonist receptor activities and have been used in migraine therapy. Without being bound by any particular theory, it is believed that the efficacy of ergots in relieving migraine arises, in part, from pharmacological activity distinct from the recognized 5-HT1 agonist property. Particular reference is made to ergotamine tartrate, ergonovine maleate, and ergoloid mesylates (i.e. dihydroergocornine, dihydroergocristine, dihydroergocryptine (dihydro-α-ergocryptine and dihydro-β-ergocryptine), and dihydroergotamine mesylate.

Some of these agents are not reliably effective treatments for migraine. However, some agents are useful in the treatment of migraine, but after an initial therapeutic effect in some patients, migraine symptoms are seen again within about 1–24 hours after the initial relief. That is, after a dosage of a therapeutic agent has been administered to a subject in an amount to effectively treat a migraine, and migraine palliation has been observed, migraine symptoms occur again from as soon as about 1–8 hours after first relief to about 12 to 24 hours later. It will be appreciated that individual migraineurs display individualized symptoms and timing for this phenomenon as will treatment with particular therapeutic agents.

In some forms of migraine, certain patients have found total or partial relief with the use of analgesics such as acetaminophen and phenacetin and other non-steroidal non-opiate analgesics not generally classified as anti-inflammatory. While, these agents, when taken alone, are rarely effective in providing complete and rapid relief of all the symptoms of migraine, especially when the symptoms of the attack already include nausea or vomiting, in combination therapy of the present invention their effectiveness is surprisingly increased.

As outlined by K. M. A. Welch (*New Eng. J Med*, 1993:329; 1476–1483), the initial dosages of the analgesics useful for the treatment of migraine are: aspirin, 500–650 mg; acetaminophen, 500 mg; naproxen sodium, 750–825 mg; tolfenamic acid, 200–400 mg; and, ibuprofen 200 mg. After oral dosing, peak plasma concentrations in subjects not experiencing a migraine attack usually occur at or about 1 hour for aspirin and acetaminophen, and between 1–2 hours for naproxen sodium, tolfenamic acid, and ibuprofen.

The headache, which occurs under the circumstances described above, has been variously and interchangeably termed a "rebound," "relapse," "recurrent," or "secondary" headache. The terms not withstanding, it is presently unknown as to whether this later headache is a continuation of the physiological chain of events that caused original headache, or a new headache due to other or repeated but unrelated underlying pathology. It is also possible that the follow on headache is a response to therapeutic agents which initially were successful in treating the initial migraine symptoms. The terms "rebound", "relapse," "recurrent" and "secondary" (as defined below) are considered synonymous as used herein without inferring a mechanism or cause of the headache described above.

It has been reported that of the 50 to 70% of patients who experience migraine symptom relief within 2 hours from initial dosing with a 5-HT agonist, 30–50% experience migraine symptoms again within the next 1–24 hours. In view of the extreme discomfort and long duration of pain that characterizes migraine headaches, a therapy that reduces or avoids rebound migraine is of substantial importance.

Note is made of certain studies illuminating aspects of migraine therapy and of observed recurrent headache after treatment with a 5-HT agonist, the teachings of which are incorporated by reference.

1. Sumatriptan-A reappraisal of its pharmacology and therapeutic efficacy in the acute treatment of migraine and cluster headache. Plosker G L et al.; *Drugs* 1994;47:622–655
2. Subcutaneous Sumatriptan in a clinical setting: The first 100 consecutive patients with acute migraine in a tertiary care center. Sheftell F D et al.; *Headache* 1994;34:67–72
3. Migraine and cluster headache—their management with sumatriptan: a critical review of the current clinical experience. Wilkinson M et al.; *Cephalalgia* 1995;15:337–357
4. Treatment of the migraine attack. Silberstein S D; *Current Opinion in Neurology* 1994;7:258–263
5. Drug therapy of migraine. Welch K M A; *New Eng. J Med*; 1993;329: 1476–1483
6. Recent advances in the acute management of migraine and cluster headaches. Kumar K L; *J Gen Int Med* 1994;9:339–348

SUMMARY OF THE INVENTION

This invention comprises a method of treating migraine in a human comprising co-timely administering of a therapeutically effective amount of a 5-HT agonist coordinated with a therapeutically effective amount of an NSAID or non-NSAID analgesic, and particularly a long-acting NSAID. In some embodiments, an additional NSAID or non-NSAID analgesic is also employed in co-timely coordinated administration. Particular note is made of ibuprofen or aspirin, each with quick onset. Particular note is further made of the non-NSAID analgesic acetaminophen. Particular attention is drawn to the method of this invention wherein the 5-HT agonist is sumatriptan. In some embodiments of this method sumatriptan administered in an amount of from about 0.01 and further from about 1 to about 300 mg, and, optionally, administration is oral, intranasal, rectal, sub-lingual, injected, inhaled or buccal. In particular embodiments wherein administering of sumatriptan is parenteral, the administered amount is about 1 to about 10 mg. For subcutaneous sumatriptan, injecting so as to establish a peak blood level of from about 1 to about 150 ng/ml is contemplated, with specific reference to a peak blood level from about 10 to about 90 ng/ml, and more specifically from about 10 to about 70 ng/ml. Pharmacologically and pharmacokinetically comparable blood levels are particularly noted embodiments for other 5-HT agonists.

In the claimed method, naproxen, or pharmaceutically acceptable salt thereof is a useful NSAID, and particularly naproxen sodium, and further when the 5-HT agonist is sumatriptan. In this method naproxen or pharmaceutically acceptable salt thereof is administered to a human in an amount of from about 100 mg to about 1500 mg, with particular reference to from about 100 mg to about 1500 mg, and more particularly from about 200 to about 600 mg. Pharmacologically and pharmacokinetically comparable doses are particularly noted embodiments for other NSAIDs and non-NSAID analgesics.

In further embodiments of the method of coadministering sumatriptan with naproxen or pharmaceutically acceptable salt thereof (e.g., naproxen sodium) is establishing a blood plasma level of from about 10 to about 150 mcg/ml of blood, and optionally from about 30 to about 80 mcg/ml.

In particular embodiments of the claimed method an 5-HT agonist and an NSAID or non-NSAID analgesic are administered simultaneously, either as separate formulations or combined in a unit dosage form.

This invention is directed to both the method of treating migraine as noted and to the specific dosage form, which is, optionally a quick dissolve tablet, trochee, capsule, caplet, dragee, or lozenge. Particular quick dissolve formulations include the 5-HT agonist sumatriptan and the NSAID naproxen, and further wherein the unit dosage form comprises from about 5 to about 100 mg. sumatriptan, and from about 200 to about 600 mg naproxen.

The method of this invention also includes administering a therapeutically effective amount of NSAID as measured subject blood levels is reached by at least about 1 hour after 5-HT agonist administration and maintained for at least about 12 hours after 5-HT agonist administration.

In yet another embodiment, the invention includes a method of treating migraine in a human comprising a combination drug therapy of co-timely administration in the treatment of rebound headache by providing a rebound headache preventing therapeutically effective amount of a 5-HT agonist coordinated with a rebound headache preventing therapeutically effective amount of a long-acting NSAID or other analgesic or combination of NSAID and other analgesic.

In an additional embodiment, the method of this invention comprising 5-HT agonist administration and long-acting NSAID administration, wherein at least one of said therapeutically effective amounts of either 5-HT agonist or the dose of NSAID or non-NSAID analgesic is sub-therapeutic (sub-MED) when used alone (a sub-minimal effective dose (MED) amount). Either the 5-HT agonist or the NSAID/non-NSAID analgesic is used in sub-MED amount or NSAID in sub-MED amount or both. While this does not exclude multiple 5-HT agonists and NSAIDs being used in treatment of a single subject, it is contemplated that particular embodiments will consist of a single 5-HT agonist, and a single long-acting NSAID, wherein one or both drugs are administered in sub-MED amounts.

The invention further includes a method of treating migraine in a human comprising co-timely administering of a therapeutically effective amount of a 5-HT agonist coordinated with a therapeutically effective amount of a non-NSAID analgesic such as acetaminophen. In some embodiments co-timely administering of a therapeutically effective amount of a 5-HT agonist coordinated with a therapeutically effective amount of a quick onset analgesic such as ibuprofen, aspirin or acetaminophen is useful.

DETAILED DESCRIPTION OF THE INVENTION

It has now been discovered that a combination therapy of a 5-HT agonist, including drugs structurally similar to 5-HT agonists like sumatriptan or like members of the ergot family of compounds, combined with a long acting nonsteroidal anti-inflammatory drug (NSAID) substantially reduces or eliminates the relapse phenomenon in a significant portion of migraineurs that otherwise experience relapse and that the combination of the two agents results in an enhanced therapeutic effect allowing for greater and/or longer lasting efficacy and/or lower doses than can be obtained with the conventional doses of either individual agent. Naproxen sodium is one such long acting NSAID and sumatriptan is one such 5-HT agonist.

This invention will best be understood with reference to the following definitions:

A. "Long acting" in relation to NSAIDs shall mean a pharmacokinetic half-life of at least about 4–6 hours and preferably about 8–14 hours and a duration of action equal to or exceeding about 6–8 hours. Particular reference is made to flurbiprofen with a half-life of about 6 hours; ketoprofen with a half-life of about 2 to 4 hours; naproxen and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8–9 hours; nabumetone with a half-life of about 22 to 30 hours; mefenamic acid with a half-life of up to about 4 hours; and piroxicam with a half-life of about 4 to 6 hours.

B. "Therapeutically effective amount" as to a drug dosage, shall mean that dosage that provides the specific pharmacological response for which the drug is administered in a significant number of subjects in need of such treatment. It is emphasized that migraine headache is not well understood and the etiologies of particular migraine attacks vary, as does the response to particular drugs. Thus reference to "specific pharmacological response for which the drug is administered in a significant number of subjects in need of such treatment" is a recognition that a "therapeutically effective amount," administered to a particular subject in a particular instance will not abort migraine onset or relieve an actual migraine headache, even though such dosage is deemed a "therapeutically effective amount" by those skilled in the art. It is to be further understood that drug dosages are, in particular instances, measured as oral dosages, or parenteral or inhaled dosages or with reference to drug levels as measured in blood.

For 5-HT agonists and NSAIDs and non-NSAID analgesics, and particularly as to those already in the marketplace, a therapeutically effective amount shall particularly include (but not be limited to) that dosage that has been determined as safe and effective for any indication. Nevertheless, in particular applications this does not exclude substantially lesser (or greater) dosages than established minimum (or maximum) dosages for which a particular 5-HT agonist or NSAID could be used to effectively treat an episode of migraine.

Particular reference is made to the following dosages of 5-HT agonists and NSAIDs, any of which are usefully combined into single dosage forms. Concerning dosages, as there is considerable variability as to the presenting condition of subjects, the skilled practitioner is expected to adjust dosages in such regard.

Sumatriptan is usefully provided as oral tablets of 25 mg, 50 mg and 100 mg and as a parenteral dosage form containing about 6 mg/ml and about 6 mg/0.5 ml for subcutaneous administration. Oral dosages of about 1–300 mg are also useful with particular reference to doses of about 10–100 mg. Peak serum levels of approximately 1–300 ng/ml are produced with doses in these ranges. Subcutaneous injections of about 1 to 8 mg of sumatriptan are useful, with particular reference to about 3 to 6 mg doses. Injections produce peak serum levels of approximately 1 to 150 ng/ml. Other dosage forms of sumatriptan include, but are not limited to, suppositories, aerosols for inhalation or intranasal administration, and nose drops, and all are contemplated in the practice of this invention.

Ergotamine tartrate in oral doses of about 1 to 5 mg with particular reference to about 1–2 mg are useful, as are doses of about 1–2 mg at 30 minute intervals, up to about 6 to 8 mg in one day. Oral inhalation of sequential doses of about 0.1 to 0.5 mg at intervals of about 5 minutes are noted, with particular reference to doses of about 0.36 mg. Suppositories of 0.1 to 5 mg with particular reference to about 2 mg are useful.

Ergonovine maleate is administrable by injection at about 0.2 mg/ml, and oral tablets of about the same strength are also administrable.

Ergoloid mesylates (i.e. dihydroergocornine, dihydroergocristine, dihydroergocryptine (dihydro-α-ergocryptine and dihydro-β-ergocryptine) are usefully provided in tablets of from about 0.2 to 2.5 mg with particular reference to about 0.5 to about 1.0 mg tablets. Such tablets contain about 0.167 mg of each of dihydroergocornine, dihydroergocristine, and dihydroergocryptine (dihydro-α-ergocryptine and dihydro-β-ergocryptine). Liquid suspensions and liquid filled capsules of about 1 mg/ml are also useful.

Concerning NSAID dosages, as there is considerable variability as to the presenting condition of subjects, the skilled practitioner is expected to adjust dosages in such regard. Nevertheless it is noted that indomethacin is particularly useful when contained in tablets of from about 25 to 75 mg, in suppositories of about 50 mg, and in oral suspensions of about 25 mg/5 ml. A typical daily oral dosage of indomethacin is three 25 mg doses taken at intervals during one day amounting to 75 mg total, though daily doses of up to about 150 mg are also useful in some subjects. Sustained release dosage forms of indomethacin are also available and provide longer lasting blood levels than conventional tablets. In particular, a 25 mg sustained release dosage form can be used as an alternative to 25 mg three times daily or 75 mg twice daily can be substituted for 50 mg three times daily.

Ibuprofen is conveniently provided in tablets or caplets of 50, 100, 200, 300, 400, 600, and 800 mg and as a suspension of 100 mg/5 ml. Daily doses should not exceed 3200 mg and doses should be individualized. In addition, 200 mg–800 mg may be particularly useful when given 3–4 times daily.

Flurbiprofen is particularly useful when contained in tablets of from about 50 to 100 mg. Daily doses of about 100 to 500 mg, and particularly about 200 to 300 mg total are useful.

Ketoprofen is particularly useful when contained in capsules of from about 25 to 75 mg. Daily doses of about 100 to 500 mg, and particularly about 100 to 300 mg are useful, as is about 25 to about 50 mg every six to eight hours.

Naproxen is particularly useful when contained in tablets of from about 250 to about 500 mg, and in oral suspensions of about 125 mg/5 ml. For naproxen sodium, tablets of about 275 or about 550 mg are particularly useful. Initial doses of about 100 to 1250 mg, and particularly 350 to 800 mg are also useful with particular note of doses of about 550 mg.

Oxaprozin is notable for having a pharmacokinetic half-life of 42–50 hours and a bioavailability of 95%. It is usefully provided as caplets of 600 mg. Daily doses of 1200 mg have been found to be particularly useful and daily doses should not exceed 1800 mg or 26 mg/kg. The lowest effective dose should always be used.

Etodolac is usefully provided in capsules of 200 mg and 300 mg and tablets of 400 mg. Useful doses for acute pain are 200–400 mg every 6–8 hours not to exceed 1200 mg/day. Patients <60kg are advised not to exceed doses of 20 mg/kg Doses for other uses are also limited to 1200 mg per day in divided doses, particularly 2, 3, or 4 times daily.

Ketorolac is usefully provided in tablets of 10 mg and as a sterile parenteral preparation for injection in 15 mg/ml and 30 mg/ml dosage forms. Oral doses of up to 40 mg with particular reference to 10–30 mg per day and parenteral doses up to 120–150 mg per day have been useful in the amelioration of pain.

Nabumetone is usefully provided in tablets of 500 mg and 750 mg. Daily doses of up to 1500–2000 mg/day after an initial dose of 1000 mg are of particular use.

Mefenamic acid is particularly useful when contained in capsules of from about 250 mg. For acute pain such as migraine, an initial dosage of about 100 to 1000 mg and particularly about 500 mg is useful, though other dosages are required for specific subjects.

Meclofenamate sodium is usefully provided as capsules of 50 mg and 100 mg. Daily doses up to 400 mg are useful and in particular doses of 50–100 mg every 4–6 hours are useful for pain relief.

Piroxicam is particularly useful when contained in tablets of from about 10 to 20 mg. It is noted that, as steady state plasma concentrations are not reached until about 7 to 12 days of dosing, prophylactic use of piroxicam is a specific avenue of therapy to establish or a plasma concentration of greater than about 5 to 6 μg/ml. In such situation, coordination and co-timely administration of an 5-HT agonist is achieved by the administration of the 5-HT agonist approximately at the onset of a migraine.

Useful dosages of other analgesics to combine with 5-HT agonists include aspirin (particularly about 325–1000 mg and 500–650 mg), phenacetin, and acetaminophen (particularly about 325–1000 mg). The rapid absorption of acetaminophen in about 30 to 60 minutes and the plasma half-life of about 2 hours are noted. In the practice of this invention, the combination of 5-HT agonist with one or more NSAIDs or other analgesics (non-NSAID analgesics) is particularly contemplated. In particular pharmaceutical applications such as those subjects who do not usually experience rebound headache, the rapid relief aspect of a short onset analgesic directs the use of a dosage of a 5-HT agonist with such analgesics as acetaminophen or ibuprofen or both. Other combinations such as a 5-HT agonist, acetaminophen and naproxen sodium, or 5-HT agonist, ibuprofen and naproxen sodium are contemplated.

C. "Co-timely" as to drug administration shall mean administration of a second drug for migraine relief while a first drug for migraine relief is present in a therapeutically effective amount. It is to be understood that in some instances this will require sequential administration. In some instances, multiple routes of administration will be employed such as intravenous or subcutaneous injection of an 5-HT agonist, while a long acting NSAID is taken orally from prior to or subsequent to such 5-HT agonist injection.

D. "Coordinated" in the practice of the present invention combining 5-HT agonist and NSAID administration shall mean administration of an NSAID such that effective plasma levels of the NSAID will be present in a subject from about one hour to about 12–24 hours after the onset of migraine or onset of precursor symptoms of a migraine. In some embodiments this will be about 1 to 12 hours after a 5-HT agonist has been administered. The coordination time is clearly related to the route of NSAID administration. That is, for example, i.m. routes will generally have shorter lead times to peak plasma level than oral routes. With oral NSAID formulations, it is noted that the time to peak plasma levels for particular NSAIDs is as follows: flurbiprofen peaks in about 1 to 2 hours; ketoprofen peaks in about one-half to 2 hours; naproxen and naproxen sodium peak at about 2 to 4 hours and 1 to 2 hours respectively; oxaprozin peaks at about 3 to 5 hours; etodolac peaks at about 1 to 2 hours; indomethacin peaks at about 1 to 4 hours; ketorolac peaks at about one-half to 1 hour; nabumetone peaks at about 2.5 to 4 hours; mefenamic peaks at about 2 to 4 hours; meclofenamate peaks in 0.5–1 hours; and piroxicam peaks at about 3 to 5 hours.

E. "5-HT agonist" is to be broadly understood to include 5-HT agonists of all types, including but not limited to 5-HT1-like agonists, 5-HT1B, and 5-HT 1D agonists. Particular reference is made to sumatriptan succinate and related 5-HT agonist heterocyclic compounds described in U.S. Pat. No. 4,816,470 to Dowle et al.; ergot alkaloids and related compounds such as dihydroergotamine mesylate (DHE 45), ergotamine tartrate, ergonovine maleate, ergoloid mesylates (i.e. dihydroergocornine, dihydroergocristine, dihydroergocryptine (dihydro-α-ergocryptine and dihydro-β-ergocryptine); Pfizer CP-93129 as described in European Patent Application 379314 (the teachings of which are incorporated herein by reference), and Allelix ALX 1323; Merck L 741604; SmithklineBeecham SB 220453; and Almirall LAS31416, zolmitriptan GlaxoWellcome licensed to Zeneca; and naratriptan to GlaxoWellcome. In addition, other pharmacologically related compounds are contemplated as within the ambit of this invention.

F. "Relapse headache" variously and interchangeably termed a "rebound, relapse, recurrent or secondary" headache shall mean headaches experienced most notably by that portion of the migraineur population that, while experiencing initial relief (or avoidance of migraine in the case of treated precursor symptoms) upon administration of a 5-HT agonist, experience return of migraine or migraine symptoms within the next about 1 to 24 hours. As noted above, this group comprises perhaps 40% of those subjects that experience returns of migraine or migraine symptoms, whom initially respond to 5-HT agonist therapy. Although it is presently unknown if this is a continuation of the original headache, a new headache either due to the ongoing underlying pathology or perhaps related to the administration of the therapeutic agents used initially to treat the migraine symptoms, these terms will be considered synonymous as used herein without inferring a mechanism or cause of the secondary headaches described above.

"Rebound moderated" as to sumatriptan shall mean that at least about 20% of that 40% will not experience recurrence of migraine within the 24 hours subsequent to "initial migraine relief" as defined below, which translates into an 8% overall improvement in the response of an entire group. As to ergots, rebound moderated shall mean a statistically significant improvement in return of migraine or migraine symptoms.

G. "Initial migraine relief" shall be understood to be the reduction or abolition of migraine symptoms from first onset of either a migraine attack or the precursor indicia of a migraine headache such as the aura and visual "scotoma" in about a 24 hour period.

H. "Unit dosage form" shall mean single drug administration entity. By way of example, a single tablet, capsule, dragee, or trochee, suppository, or syringe combining both an 5-HT agonist and an NSAID would be a unit dosage form. Administration of a unit dosage form will result in blood levels of the NSAID required to produce a therapeutic effect within about the first hour after dosing and will still be present at least about 8–12 hours after initial dosing, and in particular instances, for as long as about 24 hours after dosing. Blood levels of the 5-HT agonist normally associated with a therapeutic effect will be present within the first hour and should persist in measurable quantities for at least about 4–6 hours. In the particular example of the NSAID naproxen sodium about 550 mg combined with the 5-HT agonist sumatriptan of about 25 mg, results in blood levels of naproxen ion of approximately 40 mcg/ml within 1 hour after dosing and blood levels exceeding approximately 20 mcg/ml present about 12 hours after dosing and, in particular instances, as long as about 18–24 hours after dosing. Blood levels of sumatriptan will be approximately 10 ng/ml within the first hour after dosing and will remain in measurable quantities for at least about 4–6 hours.

Other combinations of these and other NSAIDs and 5-HT agonists likewise provide effective blood levels over the time periods specified above. It is preferred that the dosage form provides blood levels consistent with rapid initial migraine relief and a reduced incidence of relapse headache.

I. "Quick dissolve" in reference to a tablet or other oral dosage forms shall mean that the oral dosage form is at least about 95% dissolved within 20 minutes of administration. In determining "quick dissolve" reference is made to standard USP test methodology.

J. "Enhanced therapeutic effect" in the context of this invention shall mean that the initial relief of migraine symptoms will occur more quickly with a claimed combination of two agents compared to the same doses of each component given alone; or that doses of one or both component(s) below what would otherwise be a (apparently) minimum effective dose (a "sub-MED").

While the experienced clinician is able to monitor and adjust dosages as to each subject relative to the severity of the migraine attack and the presence of side-effects, generally available information on maximum common daily dosages of NSAIDs is useful as a cautionary guideline. In particular instances, however, exceeding these "maximum" doses is the therapeutic choice of the medical professional, it is noted that an indication of maximum daily doses in milligrams is as follows; flurbiprofen 300; ketoprofen 300; naproxen 1500, naproxen sodium 1375; oxaprozin 1800; etodolac 1200; indomethacin 150 to 200; ketorolac 120 mg i.m. and 40 oral; nabumetone 2000; mefenamic acid 1000; and piroxicam 20.

Without being bound by any particular theory, it is believed that by combining a 5-HT agonist with a long-acting NSAID one can achieve an enhanced therapeutic effect initially (within the first 6 hours) and a lower incidence of relapse headaches within the first 24 hours after initial dosing.

Furthermore, the enhanced therapeutic effect is achievable with sub-MED doses of one or both of these therapeutic agents which provides the additional benefit of reduced incidence of side effects associated with either or both agents. For example, combining ergotamine tartrate 0.5 mg (a sub-MED, instead of the standard dose of 1–3 mg) with 125–550 mg naproxen sodium will, in some instances, provide migraine relief with a lower incidence of adverse events such as cardiovascular complications, nausea, or ergotism, and lower risk of such effects in a given subject. Another example is the combination of sumatriptan 5–15 mg (instead of the usual minimum recommended dose of 25–100 mg) plus naproxen sodium 125–550 mg. In this example, the therapeutic effect is excellent with a lower incidence of adverse events such as cardiovascular complications, weakness, tingling, warm and hot sensations, and chest discomfort. A third example is the use of sumatriptan injection 1–4 mg (instead of 6 mg which is the commonly recommended dose) combined with a suitable dose of naproxen sodium, either orally or by another route. In this instance, a significant reduction in sumatriptan side effects such as, but not limited to, tingling, weakness, flushing, asthenia, chest and upper body pressure and discomfort and the risk of cardiovascular complications is accompanied by excellent and long-lasting relief similar or superior to what one normally achieves with the 6 mg injection.

While not being bound by any particular theory, sumatriptan and other 5-HT agents, including those of the ergot structure, are thought to exert their beneficial effect in migraineurs by either reducing the release of pro-inflammatory mediators around certain nerves and blood vessels or by vasoconstriction of selected blood vessels in the head or both. However, they are thought to be devoid of analgesic activity and it is believed that their pharmacologic actions are dependent upon reaching and/or maintaining certain blood concentrations and that these concentrations are relatively short-lived. Relapse within the first 24 hours is well documented and occurs in up to 40–50% of patients who initially obtain relief but the cause is unknown.

NSAIDs such as naproxen sodium are thought to relieve migraine pain through their known analgesic action, but may also relieve symptoms by reducing the neurogenic and vascular inflammation secondary to their known anti-inflammatory actions or by other mechanisms such as, but not limited to, platelet inhibition or inhibition of prostaglandin synthesis. In addition, naproxen and naproxen sodium have half-lives on the order of 12–15 hours and produce a long-lasting effect.

While not being bound by any particular theory, it is believed that the "relapse" headache often associated with 5-HT agonists is due to the original beneficial effect of the 5-HT agonists wearing off because of their short duration of action while a) the underlying trigger for the original migraine episode is still present and/or b) while the causative agent for the pain and other symptoms, presumably the vascular and/or neurogenic inflammation, still exists. It is also possible that the relapse is due to an unknown mechanism including some as yet unappreciated property of 5-HT agonists.

In this context, the addition of a long-acting NSAID to a 5-HT agonist extends the period of effective anti-migraine action and prevents the relapse headache for occurring (or "rebound moderates"), whatever is its cause. In addition, because NSAIDs and 5-HT agonists, including those of both the 5-HT like structure and the ergot structure, have different pharmacologic properties and may relieve migraine through their own unique mechanisms, in some instances their combined use results in a greater beneficial therapeutic effect compared with the effect one achieves with the same doses of each agent used singly.

The present invention further provides a method of screening and diagnosing subjects that are subject to the vascular and/or neurogenic inflammation associated with subpopulations of migraineurs which experiences rebound headaches treatable by the present invention. As identified, this population is amenable to migraine prophylaxis tailored to such physiology, which a variety of therapies including, in some embodiments, maintenance levels of NSAID administration.

EXAMPLE 1

An adult female migraineur complains of a migraine attack consisting of typical migraine headache, nausea and sensitivity to light and sound. She is dosed with a single oral tablet containing sumatriptan 25 mg and naproxen sodium 550 mg. Her symptoms start to diminish within one hour and by three hours she is completely symptom free. No relapse over the next 48 hours is reported. Her pain is relieved more quickly and with longer uninterrupted relief than when she takes either agent alone.

EXAMPLE 2

An adult female migraineur is complaining of a migraine attack consisting of typical migraine headache, nausea and sensitivity to light and sound. She is dosed with a single subcutaneous injection of sumatriptan 6 mg and at the same time orally ingests a tablet containing naproxen sodium 550 mg. Her symptoms start to diminish within 20 minutes and by two hours she is completely symptom free and has no relapse over the next 24 hours. Her pain is relieved more quickly and with longer uninterrupted relief than when she takes either agent alone.

EXAMPLE 3

An adult female migraineur is complaining of a migraine attack consisting of typical migraine headache, nausea and sensitivity to light and sound. She is dosed with a single oral tablet containing sumatriptan 12.5 mg and naproxen sodium 550 mg. Her symptoms start to diminish within one hour and by three hours she is completely symptom free and has no relapse over the next 48 hours. Her pain is relieved more quickly and with longer uninterrupted relief than when she takes either agent alone. She experiences fewer adverse sumatriptan drug reactions than if she receives standard (higher) doses of sumatriptan, with particular reference to asthenia and flushing.

EXAMPLE 4

An adult female migraineur, with a history of relapse headache in 6 to 24 hours when dosed with 6 mg sumatriptan alone, is complaining of a migraine attack consisting of typical migraine headache, nausea and sensitivity to light and sound. She is dosed with a single subcutaneous injection of sumatriptan 2 mg and orally ingests a tablet containing naproxen sodium 550 mg. Her symptoms start to diminish within 30 minutes and by two hours she is completely symptom free and has no relapse over the next 48 hours. She experiences fewer adverse sumatriptan drug reactions than if she receives standard (higher) doses of sumatriptan, with particular reference to asthenia and flushing, chest discomfort, as compared reaction to with sumatriptan 6 mg injections.

EXAMPLE 5

A male 25 years of age offers the same presenting history and indication as in Example 4. With the same treatment, the same result is obtained.

EXAMPLE 6

A variety of combinations of 5-HT agonists and NSAIDs can be made into a single dosage form, either tablet, capsule, suppository, injections or other. As an example, a rapidly dissolving tablet of 0.5 mg ergotamine tartrate combined with naproxen sodium 550 mg is conveniently available for use. Another example includes a rapidly dissolving tablet of 12.5 mg of sumatriptan combined with 550 mg of naproxen sodium. Particular note is made of binding agents such as pregelatinized maze starch, polyvinylpyrrolidone or hydroxypropyl methylcellulose; fillers (e.g. lactose, microcrystalline cellulose or calcium phosphate, disintegrants (potato starch, croscarmellose sodium, or sodium starch glycollate) ;wetting agents (e.g. sodium lauryl sulphate)or other agents suitable for tableting.

The 5-HT agonist and NSAID combined compositions can be made up of various agents listed herein. As an example, in the case of naproxen sodium and sumatriptan, several tablet strengths are available including, but not limited to, 12.5 mg sumatriptan/550 mg naproxen sodium, 25 mg sumatriptan/550 mg naproxen sodium, 12.5 mg sumatriptan/275 mg naproxen sodium, 25 mg sumatriptan/ 275 mg naproxen sodium. Each tablet dissolves within 20 minutes rapidly producing effective blood levels of each component as listed herein.

The 5-HT agonist and NSAID combined compositions of this invention possess valuable pharmacological properties. They effect long term migraine attack relief with substantially reduced incidence of relapse migraine headache. In some instances, they provide initial migraine relief with a reduced incidence of side effects, and/or greater efficacy. This effect can be demonstrated, for example, using the methods employed in the clinical studies reviewed by Plosker and McTavish, (*Drugs* 1994;47:622–651), Wilkinson et al. (*Cephalalgia* 1995;15:337–357), and Visser et al. (*Cephalalgia* 1996;16:264–269) the teachings of which are incorporated herein by reference.

Thus, these combination compositions (or separate use of both 5-HT agonist and NSAID) can be used in normal and in particularly recalcitrant migraine disease therapy.

The pharmacologically active compositions of this invention can be processed in accordance with conventional methods of Galenic pharmacy to produce medicinal agents for administration to patients, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc.

It is also possible to freeze-dry the new compositions and use the lyophilizates obtained, for example, for the preparation of products for injection.

Generally, the compositions of this invention are dispensed in unit dosage form comprising 1–100 mg of sumatriptan or equivalent doses of other 5-HT agonists and 200–600 mg of naproxen sodium or equivalent doses of other NSAIDs in a pharmaceutically acceptable carrier per unit dosage.

It will be appreciated that the actual preferred amounts of active compositions in a specific case will vary according to the specific compositions being utilized, the particular compositions formulated, the mode of application, and the particular route of administration. Dosages for a given subject can be determined using conventional considerations, e.g., by customary comparison of the differential activities of the subject compositions and of a known agent, or by means of an appropriate, conventional pharmacological protocol.

I claim:

1. A method of treating migraine in a human comprising co-timely administering of a therapeutically effective amount of a 5-HT agonist coordinated with a therapeutically effective amount of an NSAID or non-NSAID analgesic, wherein said therapeutically effective amounts are sub-MED amounts.

2. The method of claim 1 wherein the NSAID is a long-acting NSAID.

3. The method of claim 1 wherein the 5-HT agonist is sumatriptan.

4. The method of claim 3 wherein the 5-HT agonist is sumatriptan non-parenterally administered in an amount of from about 1 to about 15 mg.

5. The method of claim 4 wherein administering is orally, intranasally, rectally or sublingually.

6. The method of claim 3 wherein sumatriptan administering is parenterally from about 1 to about 4 mg.

7. The method of claim 6 wherein administering is by subcutaneous injecting.

8. The method of claim 2 wherein the NSAID is naproxen, or pharmaceutically acceptable salt thereof.

9. The method of claim 3 wherein the NSAID is naproxen, or pharmaceutically acceptable salt thereof.

10. The method of claim 9 wherein the naproxen or pharmaceutically acceptable salt thereof is administered to a human in an amount of about 200 mg or less.

11. The method of claim 10 wherein the naproxen is administered to a human in an amount of from about 100 mg to about 200 mg.

12. The method of claim 9 wherein the naproxen is naproxen sodium.

13. The method of claim 12 wherein the naproxen is administered to a human in an amount of from about 100 mg to about 200 mg.

14. The method of claim 13 wherein the naproxen is administered in an amount of from about 100 to about 125 mg.

15. The method of claim 1 wherein the 5-HT agonist and the NSAID or non-NSAID analgesic are administered simultaneously.

16. The method of claim 1 wherein said administration is in a unit dosage form.

17. The method of claim 16 wherein the unit dosage form is a "quick dissolve" tablet.

18. The method of claim 17 wherein the 5-HT agonist is sumatriptan, the NSAID is naproxen and the unit dosage form is an oral unit dosage form comprising sumatriptan in an amount of about 15 mg or less, and naproxen in an amount of about 200 mg or less.

19. The method of claim 2 further comprising co-timely and coordinated administering of a therapeutically effective amount of at least one additional analgesic in sub-MED amount.

20. The method of claim 19 wherein the additional analgesic is ibuprofen.

21. The method of claim 20 wherein the additional analgesic is a non-NSAID analgesic.

22. The method of claim 21 wherein the additional analgesic is acetaminophen.

23. The method of claim 1 wherein the NSAID is ibuprofen.

24. The method of claim 1 wherein the non-NSAID analgesic is acetaminophen.

25. A co-timely delivery, coordinated unit dosage form comprising a therapeutically effective amount of a 5-HT agonist and a therapeutically effective amount of an NSAID or non-NSAID analgesic, wherein said therapeutically effective amounts are sub-MED amounts.

26. The unit dosage form of claim 25 wherein the NSAID is ibuprofen.

27. The unit dosage form of claim 25 wherein the NSAID is a long-acting NSAID.

28. The unit dosage form of claim 25 wherein the 5-HT agonist is sumatriptan.

29. The unit dosage form of claim 28 comprising a non-parenteral unit dosage form comprising sumatriptan in an amount of about 15 mg or less.

30. The unit dosage form of claim 29 wherein the amount of sumatriptan is about 1 to about 10 mg.

31. The unit dosage form of claim 27 wherein the NSAID is naproxen, or pharmaceutically acceptable salt thereof.

32. The unit dosage form of claim 31 comprising an oral unit dosage form comprising naproxen, or pharmaceutically acceptable salt thereof in an amount of about 200 mg or less.

33. The unit dosage form of claim 32 comprising naproxen or pharmaceutically acceptable salt thereof in an amount of from about 100 to about 200 mg.

34. The unit dosage form of claim 28 wherein the NSAID is naproxen or pharmaceutically acceptable salt thereof.

35. The unit dosage form of claim 34 comprising naproxen, or pharmaceutically acceptable salt thereof in an amount of from about 100 mg to about 200 mg.

36. The unit dosage form of claim 35 comprising naproxen or pharmaceutically acceptable salt thereof in an amount of from about 100 to about 125 mg.

37. The unit dosage form of claim 36 wherein the naproxen is naproxen sodium.

38. The unit dosage form of claim 29 wherein the 5-HT agonist is sumatriptan, the NSAID is naproxen and the unit dosage form comprises an oral unit dosage form of about 15 mg sumatriptan, and about 200 mg or less naproxen.

39. The unit dosage form of claim 25 wherein the non-NSAID analgesic is acetaminophen.

40. The method of claim 1 wherein the 5-HT agonist is a 5-HT agonist that is not an ergot alkaloid.

41. The unit dosage form of claim 25 wherein the 5-HT agonist is a 5-HT agonist that is not an ergot alkaloid.

42. The unit dosage form of claim 33 comprising naproxen or pharmaceutically acceptable salt thereof in an amount of from about 100 to about 125 mg.

43. A method of treating migraine in a human comprising co-timely non-parenterally administering sumatriptan in an amount of about from about 1 mg to about 15 mg coordinated with a non-parenterally administering naproxen or pharmaceutically acceptable salt thereof in an amount of about 200 mg or less.

44. The method of claim 43 where in the naproxen or pharmaceutically acceptable salt thereof is in an amount of from about 100 to about 200 mg.

45. The method of claim 44 wherein the sumatriptan is in an amount of about 1 to about 10 mg.

46. A non-parenteral unit dosage form comprising sumatriptan in an amount of about 15 mg or less and naproxen, or pharmaceutically acceptable salt thereof, in an amount of 200 mg or less.

47. The non-parenteral unit dosage form of claim 46 wherein said sumatriptan is present in an amount of from about 1 to about about 15 mg and said naproxen, or pharmaceutically acceptable salt thereof, is in an amount of from about 100 mg to about 200 mg.

48. The non-parenteral unit dosage form of claim 47 wherein said sumatriptan is in an amount of from about 1 mg to about 10 mg.

49. The non-parenteral unit dosage form of claim 46 wherein said naproxen or pharmaceutically acceptable salt thereof is naproxen sodium.

50. The non-parenteral unit dosage form of claim 47 wherein said naproxen or pharmaceutically acceptable salt thereof is naproxen sodium.

51. The non-parenteral unit dosage form of claim 48 wherein said naproxen or pharmaceutically acceptable salt thereof is naproxen sodium.

52. The non-parenteral unit dosage form of claim 46 wherein said sumatriptan is in an amount of from about 1 to about 10 mg.

53. The non-parenteral unit dosage form of claim 47 wherein said sumatriptan is in an amount of from about 5 to about 10 mg.

54. The non-parenteral unit dosage form of claim 46 wherein said form is an oral unit dosage form.

55. The non-parenteral unit dosage form of claim 47 wherein said form is an oral unit dosage form.

56. The non-parenteral unit dosage form of claim 50 wherein said form is an oral unit dosage form.

57. The non-parenteral unit dosage form of claim 51 wherein said form is an oral unit dosage form.

58. The unit dosage form of claim 54 wherein said form is a "quick dissolve" tablet.

59. The unit dosage form of claim 55 wherein said form is a "quick dissolve" tablet.

60. The unit dosage form of claim 56 wherein said form is a "quick dissolve" tablet.

61. The unit dosage form of claim 57 wherein said form is a "quick dissolve" tablet.

* * * * *